United States Patent
Schwab

(10) Patent No.: US 6,964,078 B2
(45) Date of Patent: Nov. 15, 2005

(54) SURGICAL INSTRUMENT AND ELECTROCAUTERY TIP-CLEANING DEVICE

(76) Inventor: Frank J. Schwab, 163 E. 81st St., Apt. 9C, New York, NY (US) 10028

(*) Notice: Subject to any disclaimer, the term of this patent is extended or adjusted under 35 U.S.C. 154(b) by 311 days.

(21) Appl. No.: 10/393,627

(22) Filed: Mar. 20, 2003

(65) Prior Publication Data

US 2003/0196289 A1  Oct. 23, 2003

Related U.S. Application Data

(60) Provisional application No. 60/374,925, filed on Apr. 23, 2002.

(51) Int. Cl.[7] .............................................. A47L 25/00
(52) U.S. Cl. ....................... 15/218.1; 15/220.4; 15/221
(58) Field of Search ........................... 15/104.5, 210.1, 15/218, 218.1, 220.4, 221, 423

(56) References Cited

U.S. PATENT DOCUMENTS

| | | | |
|---|---|---|---|
| 162,415 A | | 4/1875 | Phillippi |
| 177,394 A | * | 5/1876 | Hall et al. ................. 15/218.1 |
| 409,742 A | | 8/1889 | Fowler |
| 723,463 A | | 3/1903 | Heywood |
| 1,059,491 A | | 4/1913 | Schwartz |
| 1,223,753 A | | 4/1917 | Anderson |
| 2,029,672 A | * | 2/1936 | Rankin ......................... 33/725 |
| 2,121,307 A | * | 6/1938 | Swift ..................... 15/104.001 |
| 3,667,079 A | | 6/1972 | Hagglund |
| 3,982,357 A | | 9/1976 | Eldridge et al. |
| 4,011,693 A | | 3/1977 | Eldridge, Jr. et al. |
| 4,087,878 A | | 5/1978 | Grieshaber et al. |
| 4,361,926 A | | 12/1982 | Brush et al. |
| 4,543,751 A | | 10/1985 | Alikhan |
| 4,547,923 A | | 10/1985 | DeVries et al. |
| 4,704,760 A | | 11/1987 | Grieshaber |
| 4,752,983 A | | 6/1988 | Grieshaber |
| 4,996,800 A | | 3/1991 | Mangus |
| 5,016,401 A | | 5/1991 | Mangus |
| 5,471,705 A | | 12/1995 | Dao |
| 5,477,581 A | | 12/1995 | Wind |
| 5,666,686 A | | 9/1997 | Dao |
| 5,778,480 A | | 7/1998 | Nittinger |
| 6,021,540 A | | 2/2000 | Miller et al. |
| D435,104 S | | 12/2000 | Urueta et al. |
| 6,367,110 B1 | | 4/2002 | Urueta et al. |
| 6,402,608 B1 | | 6/2002 | Pugliesi et al. |

* cited by examiner

Primary Examiner—Mark Spisich
(74) Attorney, Agent, or Firm—Synnestvedt Lechner & Woodbridge LLP; Richard C. Woodbridge, Esq.

(57) ABSTRACT

A fine surgical instrument tip-cleaning device including a box-like cleaning unit that provides an outer abrasive cleaning surface and internal cleaning surfaces. The internal structure of the device consists of a transverse abrasive cleaning strut, which can be straddled by instruments such as forceps or bipolar cautery tips. The sidewalls of the cleaning box also contain abrasive cleaning lateral surfaces, which approximate the central cleaning strut. The lateral surfaces have a springiness, which permits the entrance of instrument tips into the box while maintaining constant contact of the abrasive cleaning surfaces against the instrument. In this fashion, effective removal of debris, coagulate and other substances are possible from surgical instruments even from the internal surfaces of forceps-type instruments. Easy introduction into the cleaning unit and back and forth motion of an instrument provides effective cleaning of the latter.

9 Claims, 6 Drawing Sheets

SURGICAL INSTRUMENT AND ELECTROCAUTERY TIP-CLEANING DEVICE

CROSS-REFERENCE TO RELATED APPLICATIONS

This application claims benefit of priority U.S. Provisional Patent Application Ser. No. 60/374,925 filed Apr. 23, 2002 and entitled "Surgical Instrument and Electrocautery Tip-Cleaning Device", by Frank J. Schwab the entire content and substance of which is hereby incorporated into this application in total by reference.

BACKGROUND OF THE INVENTION

1. Field of the Invention

This invention relates to a device having multiple cleaning surfaces for safely and effectively cleaning forceps, bipolar and uni-polar cautery device tips.

2. Description of the Related Art

The problem of maintaining clean forceps and electrocautery device tips during surgery has persisted since the time of their development. Electrocautery devices assist the surgeon in maintaining a surgical field with limited bleeding thus limiting morbidity to the patient while also permitting safer technical performance of the procedure itself. Electrocautery devices function by creating a flow of current across tissue/blood and thereby leading to electro-thermal coagulation in the area of bleeding vessels or tissue. In order for current to flow across an electrocautery device, the tip of the device must be relatively free of clotted blood, tissue and other debris.

One approach to maintaining clean cautery tips during surgery has been to manually remove debris with a surgical sponge/pad. This is not only limited in its effectiveness but poses risks of contamination and injury to the surgical team when sharp cautery tips are employed (e.g. a needle tip as used in plastic surgery for small incisions). An additional limitation of such manual cleaning remains the problem of cleaning the inner surfaces of cautery forceps that have tips, which are closely approximated.

Another approach to cleaning electrocautery device tips involves the use of what is commonly called a scratch pad. This pad consists of a disposable rectangular roughened surface (approx. 2.5×2.5 cms.) that has a spongy underside and can be attached to surgical drapes via a self-adhesive backing. Such devices are available from Johnson & Johnson, Valleylab, etc. The marked limitation of these devices involves the inability to permit cleaning of the inner aspects of electrocautery forceps and the risk of puncture by needle tip devices that may then lead to contamination if the sterile operative drapes are pierced.

There are a number of devices described in the patent literature for cleaning surgical instruments. Perhaps most relevant is U.S. Pat. No. 3,982,357 entitled "Cleaning Device for Cauterizing Knives". The Patent describes a device for cleaning cauterizing instruments such as forceps as well as knives. The forceps are placed in a cleaning unit which includes spaced, opposed abrasive strips supported by plastic pads. One embodiment, in particular, enables the simultaneous cleaning of both legs of a forceps set or the cleaning of a single blade of a knife. The device is intended to be secured by its frame with adhesive to a surgical towel or drape.

U.S. Pat. No. 4,011,693 entitled "Cleaner for Cauterizing Instruments", describes a device to be mounted to a surgical towel or drape by pressure sensitize adhesive. It is possible to convert the device between a knife cleaning mode and a forceps cleaning mode.

U.S. Pat. No. 4,543,751 describes a surgical instrument polisher and wiper. It is intended for forceps as well as cautery blades.

U.S. Pat. No. 4,087,878 describes a tool cleaning device which includes twin parallel slots.

The following patents describe the general state of the art with regard to other medical implement cleaners, polishers, and sharpeners: U.S. Pat. Nos. 3,667,079; 4,361,926; 4,547,923; 4,704,760; 4,752,983; 4,996,800; 5,016,401; 5,471,705; 5,477,581; 5,666,686; 5,778,480; 6,021,540; 6,367,110; 6,402,608 and U.S. Design Pat. D435,104.

U.S. Pat. No. 1,059,491 describes the general state of the art of a knife sharpener which includes a spring biased frame and which supports a pair of sharpening elements in a converging arrangement.

Lastly, the following patents all appear to describe the general state of the art with regard to knife sharpeners which may coincidently act as cleaners too: U.S. Pat. Nos. 162,415; 409,742; 732,463; 1,223,753 and 1,059,491.

SUMMARY OF THE INVENTION

Briefly described, the invention comprises a surgical, or electrocautery, instrument-cleaning device that is readily attachable to surgical drapes in the operative setting.

The outer shape of the device has an oval base (~4×5") unit housing a rectangular cleaning unit (similar in dimensions to an enlarged matchbox). Only one end of the cleaning unit is open as this is the cleaning portal. The cleaning unit is attached to its base positioning the opening at an angled orientation from horizontal. This offers visual and mechanical access to the cleaning portal. The base has an adhesive backing thereby permitting the operating team to affix the cleaning device to the surgical drapes in the operative setting. When applied in such a manner the cleaning device is automatically positioned with the cleaning portal directed upwards at an angle.

The cleaning device houses a set of abrasive cleaning blades, or surfaces, which are spring-loaded. They are positioned in such a manner that at the entrance of cleaning portal the surfaces are widely separated and emanate from the long box edges but then progressively become approximated to each other with distance from the portal entrance, until near contact. An additional (abrasively coated) cleaning blade (strut) traverses the device, the length of the cleaning portal opening, and just proximal to the meeting point of the larger side cleaning blades but recessed from the portal opening itself.

The cleaning device is employed by first attaching it to the operative drapes or other surface in a manner that offers easy visibility and mechanical access to the operative team. During surgery when forceps or electrocautery tips require cleaning, a simple insertion of the tips into the cleaning portal until submersion of the tips beyond the transverse cleaning strut is executed. Rapid and repeated in/out passage through the cleaning blades leads to effective removal of debris for a range of surgical and electrocautery devices including the needle tip and forcep devices. The forceps are best cleaned by placing one side of the forceps across each side of the cleaning strut (straddling), then light compression across the forceps will offer effective cleaning of the inner surfaces of the latter.

The invention may be more fully understood by reference to the following drawings.

DETAILED DESCRIPTION OF THE PREFERRED EMBODIMENT

During the course of this description like numbers will be used to identify like elements according to the different views which illustrate the invention.

Figure 1:
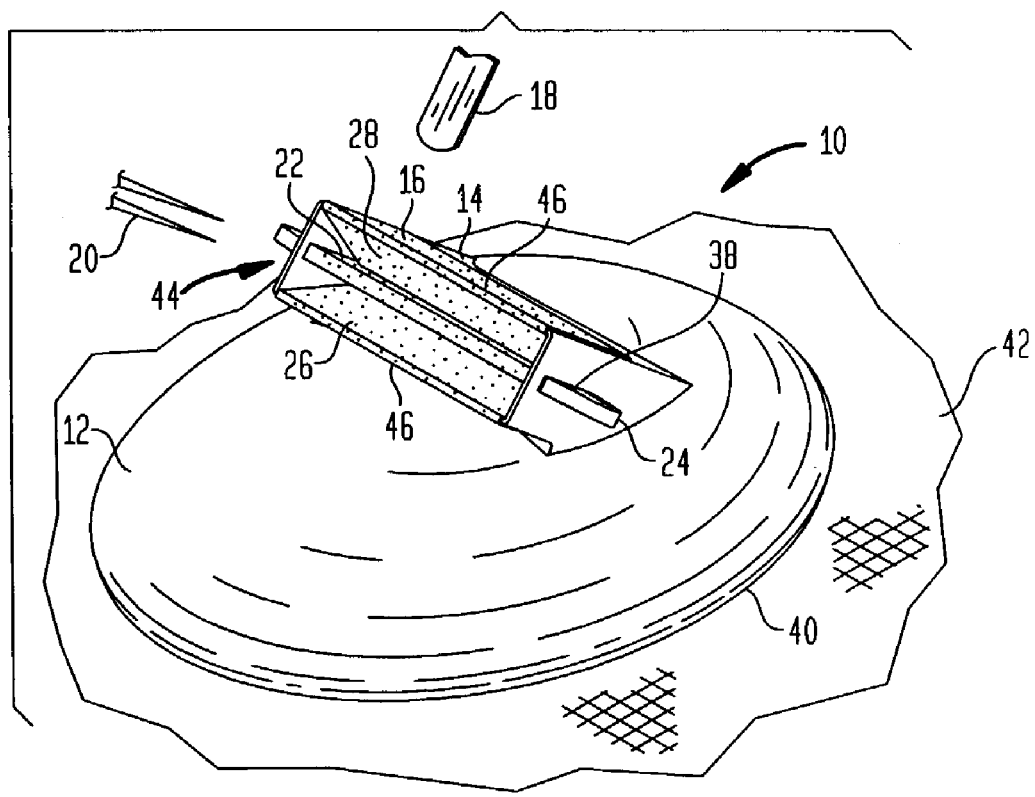
FIG. 1 is a front perspective view of the instrument cleaning apparatus shown with surgical forceps tips about to be introduced into the opening for cleaning of tissue debris and dried blood.

The preferred embodiment of the invention 10 is illustrated in FIG. 1. The device is attached via an adhesive undersurface 40 directly to surgical drapes 42 in the operative setting. The device base 12 is preferably constructed of rigid plastic. It houses and supports the cleaning unit 14. The latter has an external first, abrasive top surface 16 which permits easy cleaning of debris from a surgical instrument tip such as a cautery device (unipolar 18, or bipolar forceps 20). The cleaning unit 14 also houses a transverse cleaning strut 22 which supports abrasive surfaces permitting efficient debris and blood removal from the internal aspect of bipolar cautery tips 20 when the latter are rubbed and straddled across the strut 22 during entry into the cleaning unit 14. The transverse strut 22 is locked to the cleaning unit 14 with a locking mechanism 24 for selectively engaging the outside slots 38 in the cleaning unit housing 14. The cleaning unit 14 also houses internal abrasive cleaning surfaces 26 and 28, that are spring-loaded towards the cleaning strut 22. The passage of bipolar cautery tips 20 into the cleaning unit 14 are thus exposed to abrasive surfaces 22, 26 and 28 within and from the sides providing maximal debris/blood removal with a gliding motion in and out of the cleaning unit 14.

Figure 2:
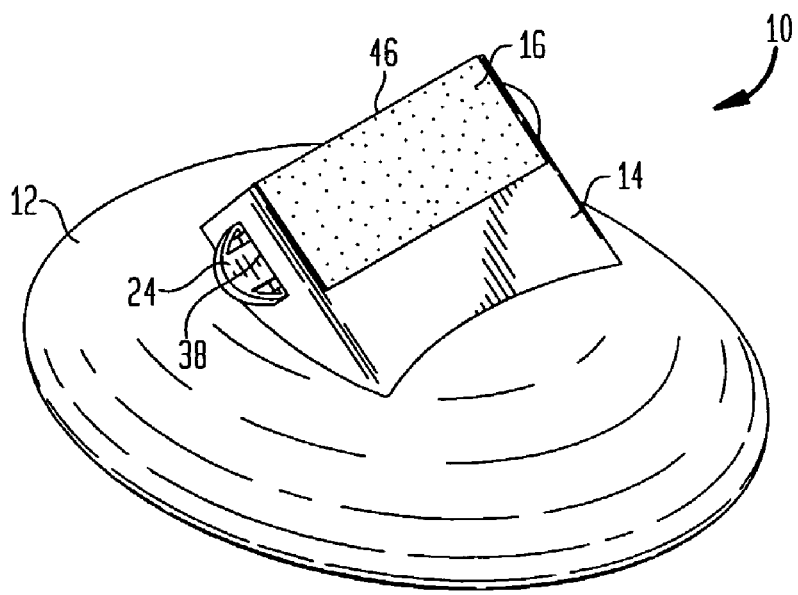
FIG. 2 is a rear perspective view of the instrument cleaning apparatus illustrated in FIG. 1.

FIG. 2 illustrates a rear perspective view of apparatus 10 from which the external abrasive cleaning surface 16 is clearly seen on the cleaning unit 14 which is housed on top of the base 12 of the device 10. The device 10 is preferably made of conventional commercial grade plastic. The external locking edge 24 of the internal cleaning strut 22 is seen engaged in slot 38 of the cleaning unit 14.

Figure 3:
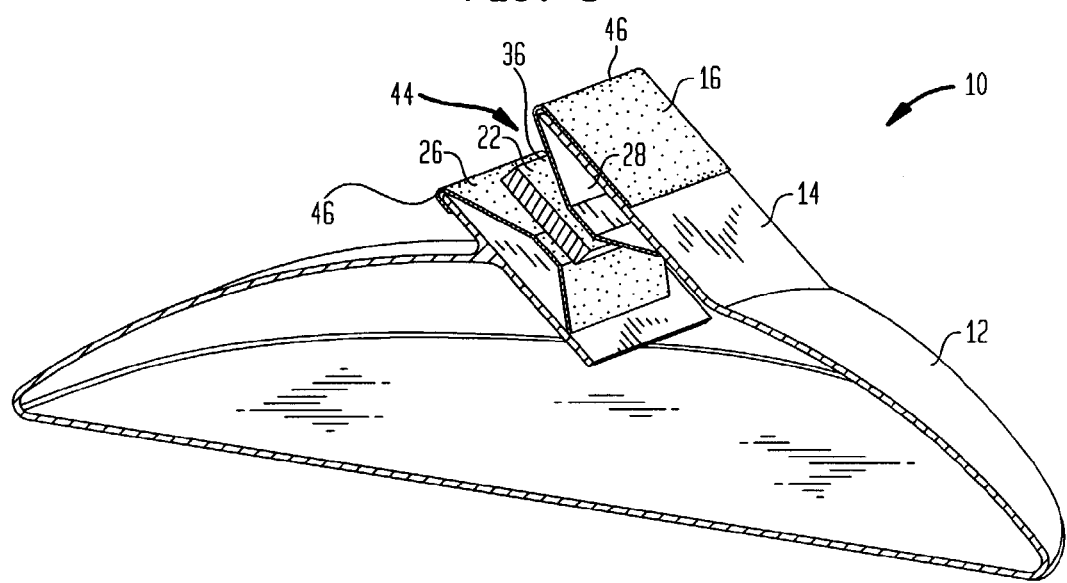
FIG. 3 is a rear, perspective cross sectional view of the preferred embodiment of the apparatus illustrated in FIGS. 1 and 2.

FIG. 3 illustrates a rear, perspective cross-section view of the device 10. The oblique orientation of the cleaning unit 14 seated within the base 12 is evident. The cleaning strut 20 is positioned across the opening or aperture 44 of the device.

One can note the superior 28 and inferior 26 lateral cleaning surfaces that approach the edge of the cleaning strut 22. Due to the supple nature of the lateral cleaning surfaces, when cautery cleaning tips 20 are passed into the cleaning unit 14, the lateral cleaning surfaces 26 and 28 are displaced but maintain pressure against the introduced instrument 22 to optimize removal of debris/blood. The cleaning surfaces 26 and 28 are preferably formed on resilient plastic so that they flex and are naturally spring biased.

Figure 4A:
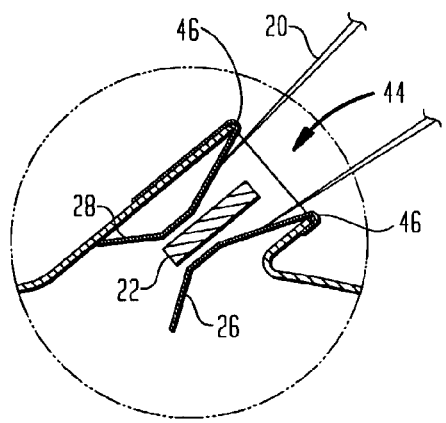
FIG. 4A is a detail, elevational cross sectional view of the cleaning unit shown in FIG. 4B.
Figure 4B:
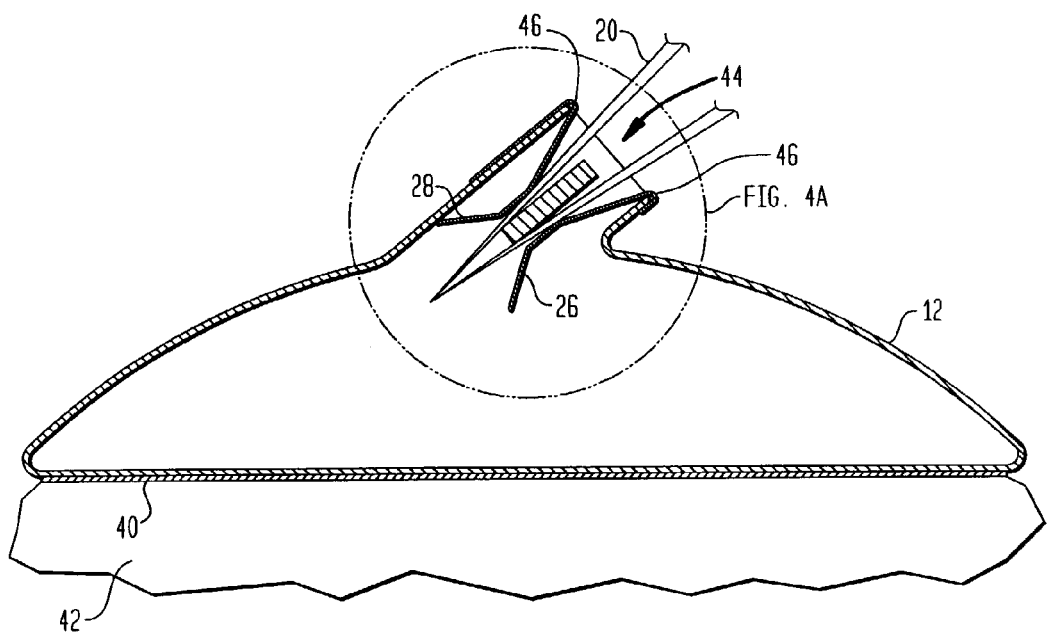
FIG. 4B is a complete, elevational cross sectional view of the surgical instrument cleaning apparatus including the region from which FIG. 4A was taken.

FIGS. 4A and 4B are cross-sectional views of the device. FIG. 4A illustrates a set of bipolar forceps tips 20 at the introduction point into the device 10. FIG. 4B illustrates the bipolar tips 20 which have been advanced into the cleaning unit, passing between the lateral cleaning surfaces 26, 28, and straddling the central cleaning strut 22. With an in-and-out motion, effective removal of debris/blood is achieved from the inner and outer surfaces of the forceps 20.

Figure 5A:
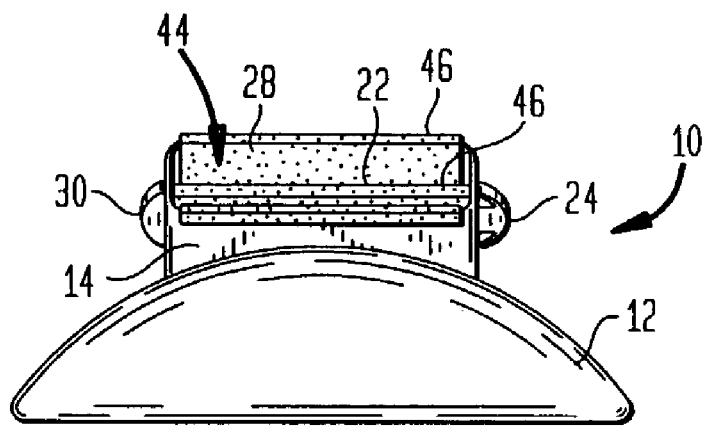
FIG. 5A is a front, end elevational view of the preferred embodiment of the apparatus illustrated in FIGS. 1–4B.
Figure 5B:
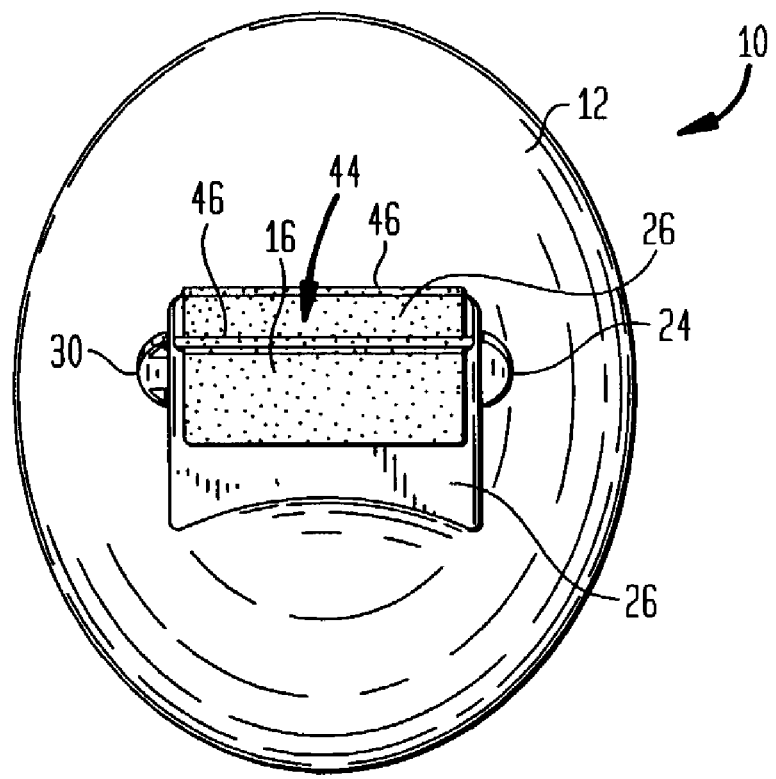
FIG. 5B is a top plan view of the preferred embodiment of the apparatus illustrated in FIGS. 1–4B.

FIGS. 5A and 5B illustrate front elevational views and top plan views of the preferred embodiment of the device 10. FIG. 5A illustrates the frontal view. The elevation of the cleaning unit 14 seated on the base 12 is seen. A view into the aperture 44 of the cleaning unit reveals the upper lateral cleaning surface 28 and the edge of the cleaning strut 22. The external locking edges 24, 30 of the internal cleaning strut 22 are seen protruding from the slots 38 in the cleaning unit 14. FIG. 5B illustrates a top plan view of the device 10. The outer cleaning abrasive surface 16 is easily seen. Looking into the entrance 44 of the cleaning unit 14, the lower lateral cleaning surface 26 is also visible.

Figure 6:
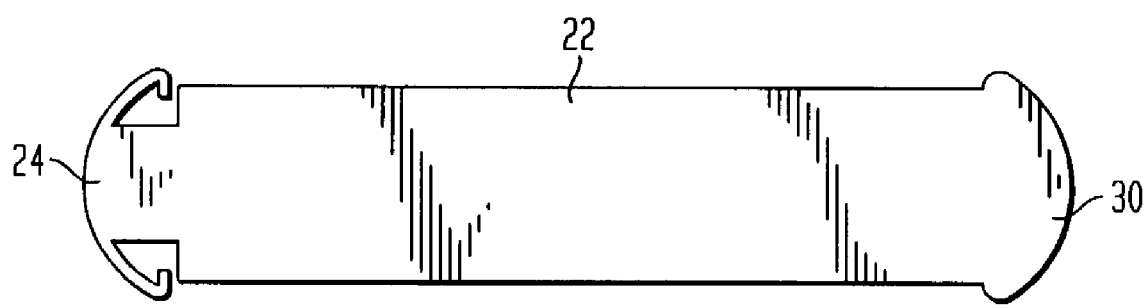
FIG. 6 is a plan view of the transverse cleaning strut located deep in the aperture of the cleaning unit.

FIG. 6 is a top plan view of the transverse cleaning strut 22. The strut 22 is very thin when seen from the side. The material is preferably plastic based and the surfaces abrasive/roughened to provide proper cleaning of surgical instruments 20 rubbed against them. The ends of the strut 24, 30 provide for locking into slots 38 of the cleaning unit 14 once the strut 22 is inserted into and across the cleaning unit housing 14.

Figure 7:
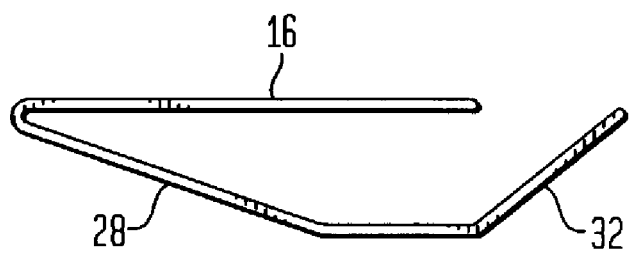
FIG. 7 illustrates a side view of one of the two internal cleaning surfaces located on the rim of the aperture of the cleaning unit.

FIG. 7 illustrates the dimensions and detailed shape of the superior lateral cleaning surface 28. The shape is practically identical to that of the inferior lateral cleaning surface 26. This section sits on the rim 46 of cleaning unit 14 such that a portion of the piece provides the outer cleaning surface 16. The lateral cleaning surface 28 is in continuity with the external cleaning surface 16. This section, at its end 32, is not joined or firmly attached to the cleaning unit 14 and thus free motion exists at that point. The lateral cleaning surface 28 consists of supple plastic with an abrasive surface. Pressure exerted against the surface 28 will lead to displacement and flattening. Through this spring-loaded type of design, a continuous pressure is possible against cautery tips 20 while they pass into the cleaning unit.

Figure 8:
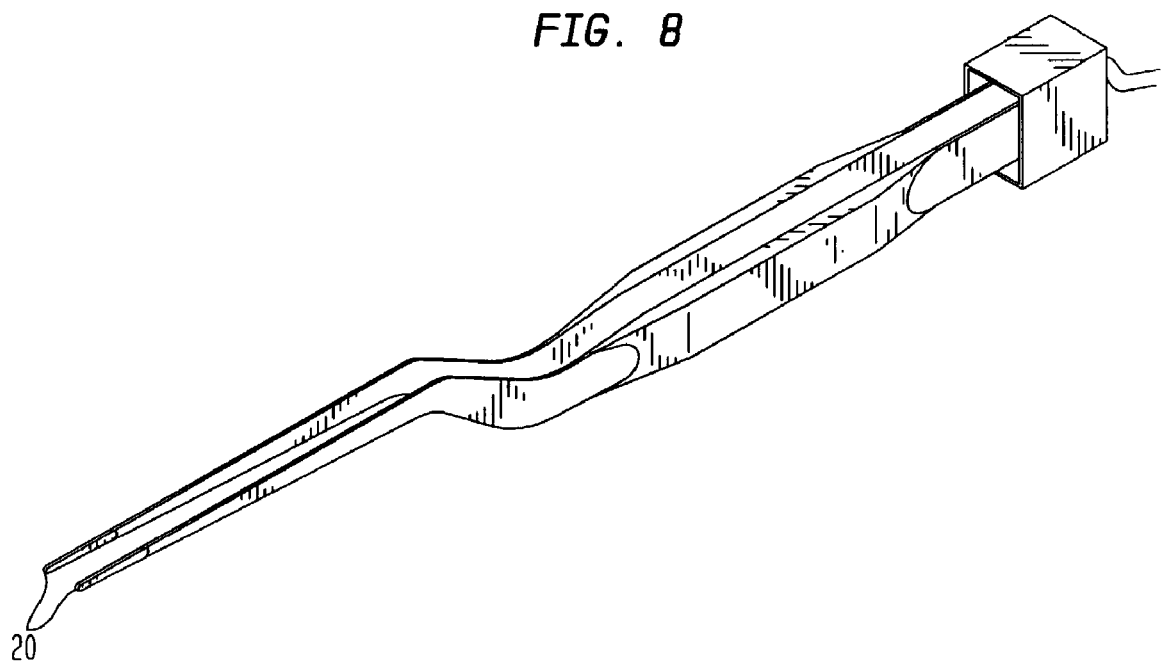
FIG. 8 is a front perspective view of a conventional pair of forceps including bipolar forceps tips.

FIG. 8 illustrates a conventional pair of forceps including bipolar cautery tips 20.

While the invention has been described with reference to the preferred embodiment thereof it will be appreciated by those of ordinary skill in the art that various modifications can be made to the invention itself without departing from the spirit and scope thereof.

What is claimed is:

1. An apparatus for cleaning the tip of a surgical instrument comprising:
   a base;
   a cleanout unit attached to said base, said cleanout unit having an aperture and a first abrasive cleaning surface located inside said aperture and resiliently attached to said cleanout unit;
   a strut section spanning said aperture; and, a second abrasive cleaning surface also resiliently attached to said cleanout unit and located inside said aperture and on the opposite side of said strut section from said first abrasive cleaning surface, wherein said strut section supports a third cleaning surface and said aperture includes an outer rim and wherein said first and second cleaning surfaces are located proximate to said outer rim and said strut section is located deeper inside of said aperture than said first and second abrasive cleaning surfaces wherein an instrument introduced into said aperture first contacts said first and second abrasive cleaning surfaces, which flex when an instrument is introduced into said aperture, before said instrument contacts said third cleaning surface located on said strut section so that insertion of said instrument into said aperture causes said instrument to contact said strut section and said first and second abrasive cleaning surfaces thereby cleaning debris off of said instrument.

2. The apparatus of claim 1 wherein said base has a substantially flat bottom suitable for placing on surgical drapes.

3. The apparatus of claim 2 further including:
an adhesive surface located on said flat bottom of said base for removably attaching said apparatus to said surgical drapes.

4. The apparatus of claim 3 further including:
slot means in said clean out unit,
wherein said strut section can be selectively inserted into said clean out unit through said slot means and selectively locked in place and then subsequently removed from said clean out unit.

5. The apparatus of claim 4 wherein said surgical instrument comprises a unipolar surgical instrument.

6. The apparatus of claim 4 wherein said surgical instrument comprise a pair of bipolar surgical forceps having cautery tips.

7. The apparatus of claim 4 wherein said clean out unit is inclined at an angle in the range of 30–70 degrees with respect to the plane of said substantially flat bottom so that it is relatively easy to insert said surgical instrument into said clean out unit.

8. The apparatus of claim 4 wherein said first and second cleaning surfaces are naturally springy so that they flex when said instrument is introduced into said aperture.

9. An apparaturs for cleaning the tip of a surgical instrument comprising:

a housing having an aperture with an outer rim therein;

a first abrasive cleaning surface attached to said housing and located inside said aperture;

a second abrasive cleaning surface also attached to said housing and located on the opposite side of said aperture from said first abrasive cleaning surface;

a strut section spanning said aperture and supporting a third cleaning surface, wherein said strut section is located deeper inside of said aperture than said first and second abrasive cleaning surfaces so that an instrument inserted into said aperture contacts said first and second cleaning surfaces before it contacts said third cleaning surface located on said strut section so that insertion of said instrument into said aperture causes said instrument to contact said third cleaning surface on said strut section and said first and second abrasive cleaning surfaces thereby cleaning debris off of said instrument.

* * * * *